(12) United States Patent
Bobrow et al.

(10) Patent No.: US 8,153,367 B2
(45) Date of Patent: *Apr. 10, 2012

(54) AMPLIFIED ARRAY ANALYSIS SYSTEM

(75) Inventors: Mark N. Bobrow, Lexington, MA (US); Karl E. Adler, Newburyport, MA (US)

(73) Assignee: Perkinelmer Las, Inc., Waltham, MA (US)

( * ) Notice: Subject to any disclaimer, the term of this patent is extended or adjusted under 35 U.S.C. 154(b) by 445 days.

This patent is subject to a terminal disclaimer.

(21) Appl. No.: 11/741,548

(22) Filed: Apr. 27, 2007

(65) Prior Publication Data

US 2007/0254308 A1  Nov. 1, 2007

Related U.S. Application Data

(63) Continuation-in-part of application No. 10/123,713, filed on Apr. 16, 2002, now abandoned, which is a continuation of application No. 09/430,429, filed on Oct. 29, 1999, now Pat. No. 6,399,299.

(51) Int. Cl.
*C12Q 1/68* (2006.01)
*C12M 1/36* (2006.01)
*G01N 15/06* (2006.01)

(52) U.S. Cl. ...... 435/6.1; 435/7.1; 435/7.72; 435/283.1; 435/287.2; 422/68.1

(58) Field of Classification Search .................. None
See application file for complete search history.

(56) References Cited

U.S. PATENT DOCUMENTS

| | | | |
|---|---|---|---|
| 4,347,311 A * | 8/1982 | Schmitz | 435/5 |
| 5,143,854 A | 9/1992 | Pirrung et al. | |
| 5,196,306 A | 3/1993 | Bobrow et al. | |
| 5,405,783 A | 4/1995 | Pirrung et al. | |
| 5,445,934 A | 8/1995 | Fodor et al. | |
| 5,486,452 A * | 1/1996 | Gordon et al. | 435/5 |
| 5,489,678 A | 2/1996 | Fodor et al. | |
| 5,525,464 A | 6/1996 | Drmanac et al. | |
| 5,583,001 A | 12/1996 | Bobrow et al. | |
| 5,700,637 A | 12/1997 | Southern et al. | |
| 5,731,158 A | 3/1998 | Bobrow et al. | |
| 5,744,305 A | 4/1998 | Fodor et al. | |
| 5,800,992 A | 9/1998 | Fodor et al. | |
| 5,871,928 A | 2/1999 | Fodor et al. | |
| 6,143,495 A * | 11/2000 | Lizardi et al. | 435/6 |
| 6,399,299 B1 * | 6/2002 | Bobrow et al. | 435/6 |
| 2003/0124583 A1 * | 7/2003 | Staab | 435/6 |
| 2003/0203372 A1 * | 10/2003 | Ward et al. | 435/6 |

OTHER PUBLICATIONS

Bobrow et al "Catalyzed reporter deposition, a novel method of signal amplification" Journa of Immunological Methods, 1991, 137: 103-112.*

* cited by examiner

*Primary Examiner* — Betty Forman
(74) *Attorney, Agent, or Firm* — Gifford, Krass, Sprinkle, Anderson & Citkowski, P.C.

(57) ABSTRACT

The present invention concerns an array-based analytical system and method having an enhanced sensitivity which allows for simple and rapid analysis of relative unmodified samples which comprises an analytical system of the type having a plurality of different first members of a specific binding pair affixed in an array thereupon, a mixture including at least one second member of a specific binding pair capable of binding to one of the first members so as to form a specific binding pair which is affixed to the support member, and a reporter system that produces a detectable signal indicative of the presence of the specific binding pair on the support member and wherein the reporter system includes an amplified reporter system that is independent of layering.

17 Claims, 6 Drawing Sheets
(1 of 6 Drawing Sheet(s) Filed in Color)

AMPLIFIED ARRAY ANALYSIS SYSTEM

RELATED APPLICATIONS

This application is a continuation-in-part of U.S. application Ser. No. 10/123,713 filed Apr. 16, 2002, which claims priority of U.S. application Ser. No. 09/430,429 filed Oct. 29, 1999.

FIELD OF THE INVENTION

This invention relates to analytical systems wherein arrays of at least one material such as oligonucleotides, DNA and/or RNA and/or fragments thereof, peptides, protein fragments, polypeptides, polysaccharides, cell fragments, cells and tissues is disposed on a support member and is contacted with a mixture which may or may not include a material which includes binding pair members which bind to at least one of the materials comprising the array. Most specifically, the invention relates to analytical systems of this type which further include an amplified reporter system that are not dependent on layering.

BACKGROUND OF THE INVENTION

Many analytical techniques and systems are based upon the ability of various materials to form a specific binding pair. As used herein, a specific binding pair is a system wherein the two components share an affinity for each other so as to cause one of the components contained in a mixture of materials to bind to the other upon contact. Either or both components of a specific binding pair may be organic or inorganic. Some examples of specific binding pairs are antibodies and antigens, nucleic materials such as DNA, RNA and fragments thereof, free nucleotides, metallic moieties and nucleic acids or proteins, metal ions-organic ligands, biotin and avidin, folic acid-folate binding protein, polysaccharides-polysaccharide binding protein, sulfhydryls and sulfhydryl reactive groups such as maleimides and haloacetyl derivatives, amines and amine reactive groups such as succinimidyl esters and isothiocyanates, etc.

Typical assays based upon the formation of specific binding pairs include a reporter system which provides a detectable signal indicative of the formation of a specific binding pair. For example, one of the members of the pair can be provided with a label which can comprise a fluorescent material, a radioactive material, any other signaling moiety, or a material which is further reactive with another species to form a colored complex or some other such detectable reaction product. The reporter system in these types of assays is commonly referred to as a layered-type system wherein successive layers of reagents such as labeled antibodies or nucleic acid probes are applied one after another in successive manipulation to generate a detectable signal.

Recently, a number of technologies have been developed which enable the production of very large arrays comprised of one or more differing materials such as oligonucleotides, DNA and/or RNA and/or fragments thereof, peptides, protein fragments, cell fragments, cells and tissues disposed upon a support body. The various members comprising the array are each capable of forming a unique, specific binding pair with their appropriate counterpart, and such arrays have great utility for rapidly screening mixtures for the presence or absence of a large number of materials. Techniques for the fabrication of such arrays will be found, for example, in U.S. Pat. Nos. 5,744,305; 5,489,678; 5,445,934; 5,405,783; 5,329,028; 5,143,854 and 4,419,444, the disclosures of which are incorporated herein by reference. The formation of specific binding pairs is detected in such arrays by utilizing conventional reporter technology, of the type described hereinabove.

There is often a need to increase the sensitivity of such assays. For example, in many instances, species will be present in the mixture at very low concentrations; hence, the detectable signal produced thereby will be very weak. Target amplification techniques, such as polymerase chain reaction (PCR) amplification may be applied to a sample containing nucleic materials so as to increase the concentration of these materials. However, PCR reaction, can be time consuming and difficult to implement. Therefore, it will be appreciated that there is a need for an array-based analytical system and method having an enhanced sensitivity which does not require such complex sample preparation or manipulation. The enhanced sensitivity of an assay of this type would allow for rapid and simple analysis of relatively unmodified biological fluids, preparations and the like. As will be described in detail hereinbelow, the present invention incorporates an amplification system into an array-based analysis. The system of the present invention may be utilized for the analysis of materials such as oligonucleotides, DNA and/or RNA and/or fragments thereof, peptides, protein fragments, polysaccharides, cell fragments, cells and tissues.

SUMMARY OF THE INVENTION

The present invention provides a method for enhancing the sensitivity of array-based analytical assay systems which comprises a support member having at least one different first member of a specific binding pair affixed in an array thereupon, a mixture which may include at least one second member of a specific binding pair capable of binding to one of the first members so as to form a specific binding pair which is affixed to the support member, and a reporter system that produces a detectable signal indicative of the presence or absence of the specific binding pair on the support member wherein the reporter system comprises an amplified reporter system that is independent of layering. A commercial reagent package capable of performing the sequence of analysis process steps is also disclosed.

BRIEF DESCRIPTION OF THE FIGURES

The patent or application file contains at least one drawing executed in color. Copies of this patent or patent application publication with color drawing(s) will be provided by the U.S. Patent and Trademark Office upon request and payment of the necessary fee.

Other advantages of the present invention will be readily appreciated as the same becomes better understood by reference to the following detailed description when considered in connection with the accompanying drawings wherein.

DETAILED DESCRIPTION OF THE INVENTION

In accord with the present invention, an array-based binding assay incorporates an amplified reporter system utilized for the analysis of various materials including oligonucleotides, DNA and/or RNA and/or fragments thereof, peptides, protein fragments, polysaccharides, cell fragments, cells and/or tissues. As used herein, an amplified reporter system means a system, in which the formation of one specific binding pair will give rise to a multitude of reporter species. This is in contrast to a nonamplified system such as a system wherein a fluorescently tagged antibody reacts with an appropriate antigen to form a specific binding pair which can include fluorescent tags or labels thereupon without generating any signal amplification from the formation of the specific binding pair.

One particularly preferred group of amplified reporter systems comprises enzymatically amplified reporter systems with catalyzed reporter deposition (CARD) being one particularly preferred amplification system. CARD amplification is a novel method of signal amplification which is disclosed in U.S. Pat. Nos. 5,731,158; 5,583,001 and 5,196,306, the disclosures of which are incorporated herein by reference. The method uses an analyte dependent enzyme activation system (ADEAS) to catalyze the deposition of reporter or hapten groups (labels) onto the solid phase of an assay support. These enzymatically deposited labels are detected directly or indirectly, which results in signal amplification and improved detection limits.

Figure 1:
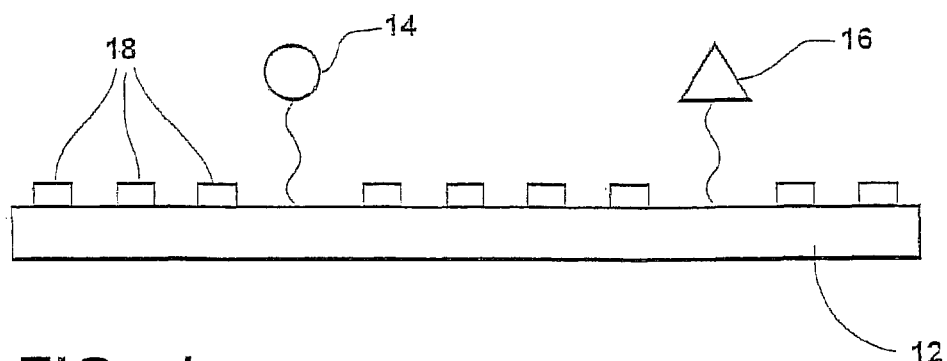
FIG. 1 is a schematic illustration of a catalyzed reporter deposition system in accordance with the present invention.

Operation of one catalyzed reporter deposition system is shown schematically in FIGS. 1-5. FIG. 1 depicts a support member 12 having an array of first members of a specific binding pair supported thereupon. The support member 12 is planar and adjacent array spots of first members are intended to be flooded with a single, binding pair member-containing solution. In contrast, prior art arrays have traditionally relied on the formation of separate analyte solution columnar volumes overlying each array spot to prevent signal interference between adjacent spots. Surprisingly, the present invention shows no appreciable signal interference in spite of the absent analyte isolation, a high degree of amplication, and small array spot sizes. As shown in FIG. 1, two members of the array 14 and 16 are depicted. As discussed above, these members can comprise materials such as oligonucleotides, DNA and/or RNA and/or fragments thereof, peptides, protein fragments, polysaccharides, cell fragments, cells, tissues, organometallic species illustratively including manganese or magnesium containing organometallics, and organic ligands capable of binding metal ions, and each is capable of binding to a specific material so as to form a specific binding pair. Organic ligands capable of chelating metal ion typically have a molecular weight of less than 500 Daltons and contain Lewis base moieties. In a typical assay, the support member 12 may be polymeric or glass and may be in the form or shape of any solid or porous support, and it will include a number of receptor sites 18 thereupon. These receptor sites 18 function to bind an activated, labeled conjugate, as will be described hereinbelow. The receptor sites 18 may comprise chemically active sites, such as phenolic sites normally present on the support member 12, or they may comprise a material separately added to the support, such as a proteinaceous material, a phenolic based material, or any other such compound capable of interacting with the activated conjugate, as will be described hereinbelow, or the support surface itself may be chemically reactive.

Figure 2:
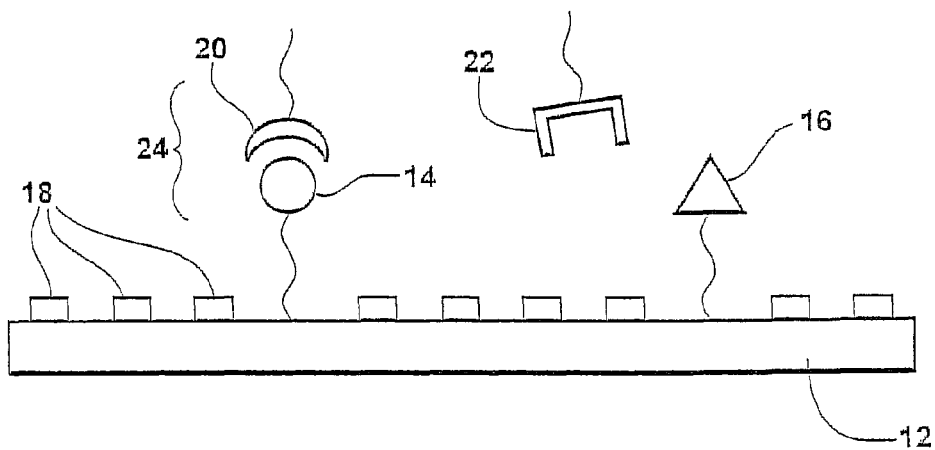
FIG. 2 is a schematic illustration of a further stage in the catalyzed reporter deposition system in accordance with the present invention.

FIG. 2 depicts a further stage in the use of the analytical system. As shown therein, the array is contacted with a mixture which may include one or more second members or analytes of a specific binding pair, capable of binding to at least one of the immobilized first members on the support 12. As specifically shown in FIG. 2, the mixture includes two different second members 20, 22. As illustrated, the second member 20 has bound to the immobilized first member 14 to form a specific binding pair 24. The other second member 22 is not capable of binding to either of the first members 14, 16, and does not form a specific binding pair, and in a subsequent step is washed away or otherwise removed from the region of the support member 12.

Figure 3:
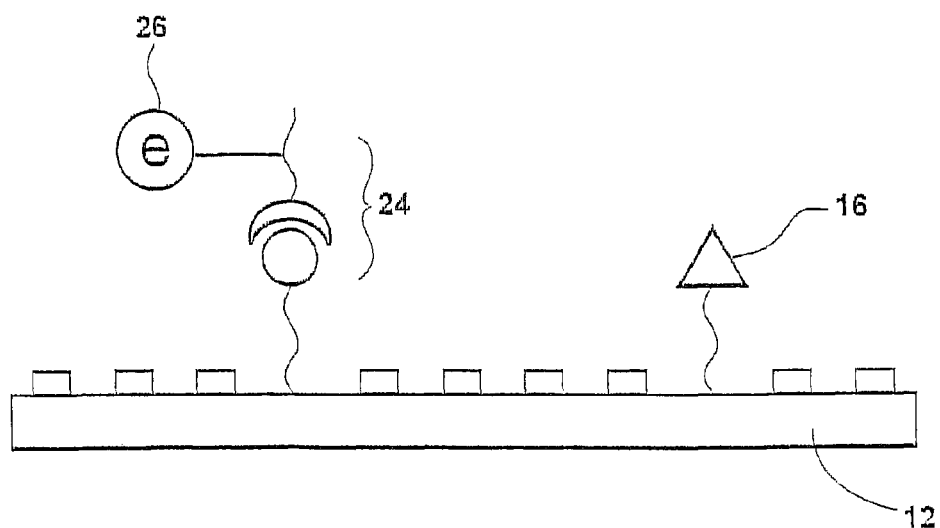
FIG. 3 is a further schematic illustration of a stage of the catalyzed reporter deposition system in accordance with the present invention.

Referring now to FIG. 3, there is shown a further step in the method. As shown therein, an enzyme 26 is coupled to the specific binding pair 24. While the Figures imply that the enzyme 26 is joined to the specific binding pair 24 after the specific binding pair is formed, the methodology of the present invention does not require this sequence of events. In some instances, the enzyme 26 may be coupled to the second member 20 prior to the formation of the binding pair, while in other instances, the enzyme 26 may be coupled after formation of the specific binding pair. Coupling can be accomplished by specific or nonspecific binding reactions. In some particular instances, the enzyme itself will be the second member of the specific binding pair, in which case, formation of the specific binding pair will inherently incorporate the enzyme. In any instance, the net result of the foregoing is that an enzyme 26 will be immobilized upon the support member 12 only at those locations in the matrix at which a specific binding pair is formed. The enzyme, in one specific embodiment, comprises horseradish peroxidase (HRP), although other enzymes may be utilized in other embodiments of the invention. Surprisingly, the free-radical nature of the reaction does not spatially spread a given array spot to proximal array spots.

Optionally, the enzyme 26 is coupled to the second member 20 directly without an intermediate bridging unit such as another antibody. Unlike usage application in the instance of ELISA (Enzyme-Linked ImmunoSorbent Assay) as evidenced in Bobrow et al. (Catalyzed reporter deposition, a novel method of signal amplification, Journal of Immunological Methods, 137:103-112, 1991), the present invention does not necessarily require a secondary antibody to form the specific binding pair 24, and therefore the secondary antibody is optionally excluded in the formation of the specific binding pair 24. It is appreciated that the recognition and detection of the first member 14 is only analyte-specific at the formation step of the binding pair 24. The attachment of the enzyme 26 to a specific binding pair such as pair 24 is universal for the detection of other different analytes such as the first member 16.

In one particular instance, the complex formed by the enzyme 26 and the specific binding pair includes only a one antibody.

Figure 4:
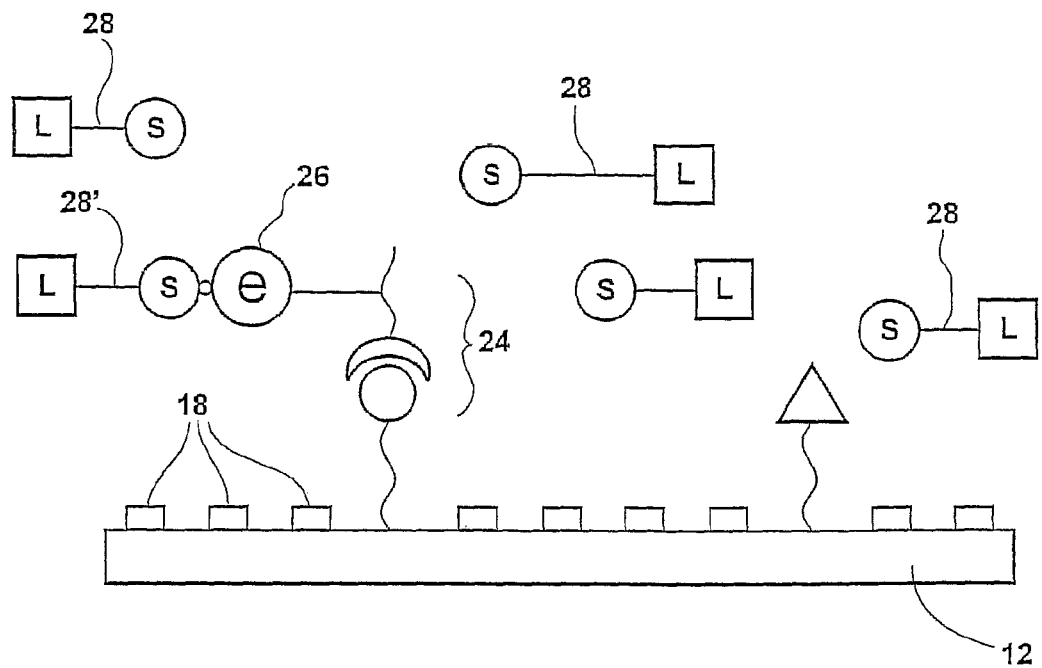
FIG. 4 is a further schematic illustration of a stage of the catalyzed reporter deposition system in accordance with the present invention.
Figure 5:
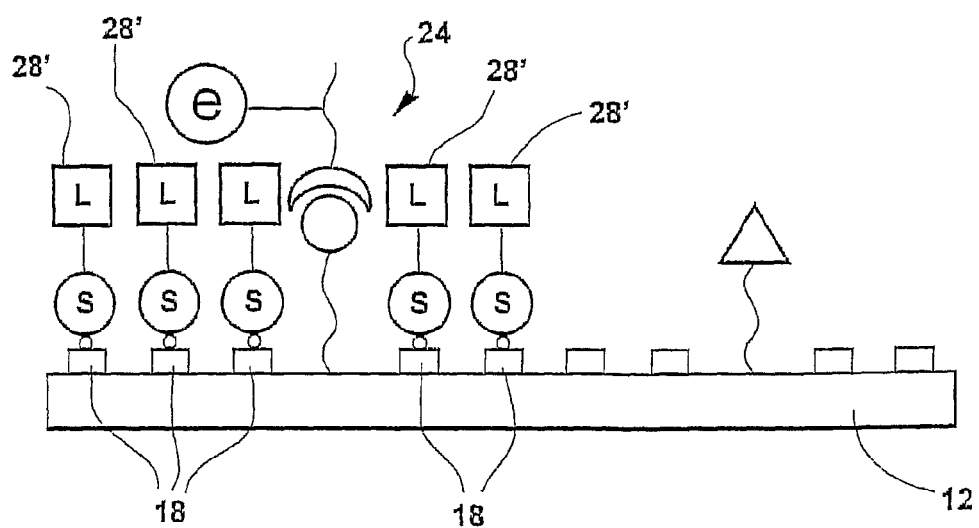
FIG. 5 is a further schematic illustration of a stage of the catalyzed reporter deposition system in accordance with the present invention.

Referring now to FIG. 4, there is shown a further stage in the operation of the analytical system of the present invention wherein the support member 12 having the specific binding pair 24 and associated enzyme 26 immobilized thereupon, is contacted with a labeled conjugate 28. The labeled conjugate 28 includes a substrate (S) for the enzyme 26, and a label (L). The substrate is a material which is activatable by the enzyme so as to cause it to bind to the receptor sites 18 on the support member 12. The receptor sites 18 may be reactive components of the support member 12 or may be added to the support member 12. The label can be any detectable label, such as a fluorescently detectable label, a hapten (e.g. biotin), a radioactive label, or a chemically reactive, color forming label, through redox, chemiluminescence or other mechanism, or any other signaling moiety. As will be seen from FIG. 4, the enzyme 26 creates an activated conjugate 28N, and as seen in FIG. 5, this activated conjugate 28N binds to the receptor sites 18 in the region of the specific binding pair 24. The unactivated conjugate 28 is not capable of binding to the receptor sites 18; hence, the label is displayed only proximate the specific binding pair 24. As noted from FIG. 5, the formation of one specific binding pair 24 catalyzes the deposition of a number of labeled conjugates, thereby providing an amplified reporter system.

The support member 12 of an inventive analytical system is pre-treated with receptor deposition. Receptors, preferably suspended or dissolved in liquid form, are deposited onto the support member in pre-determined sites thereupon. Receptors so deposited are grouped into spots in various forms such as a circular spot, a polygon spot, a square spot, or a rectangular spot, preferably a circular spot or a rectangular spot. Within each spot there contains one or more molecules of a first member such as the first member 14 or the first member 16. The spots are arranged on the support member 12 so as to provide a functional distance between any two adjacent spots. The functional distance, Fd, is the shortest distance between the boundaries of any two adjacent spots whereby signal bleeding between the two adjacent spots are prevented or minimized. The functional distance, Fd, varies with the shape of spots arranged on the support member 12.

Figure 9:
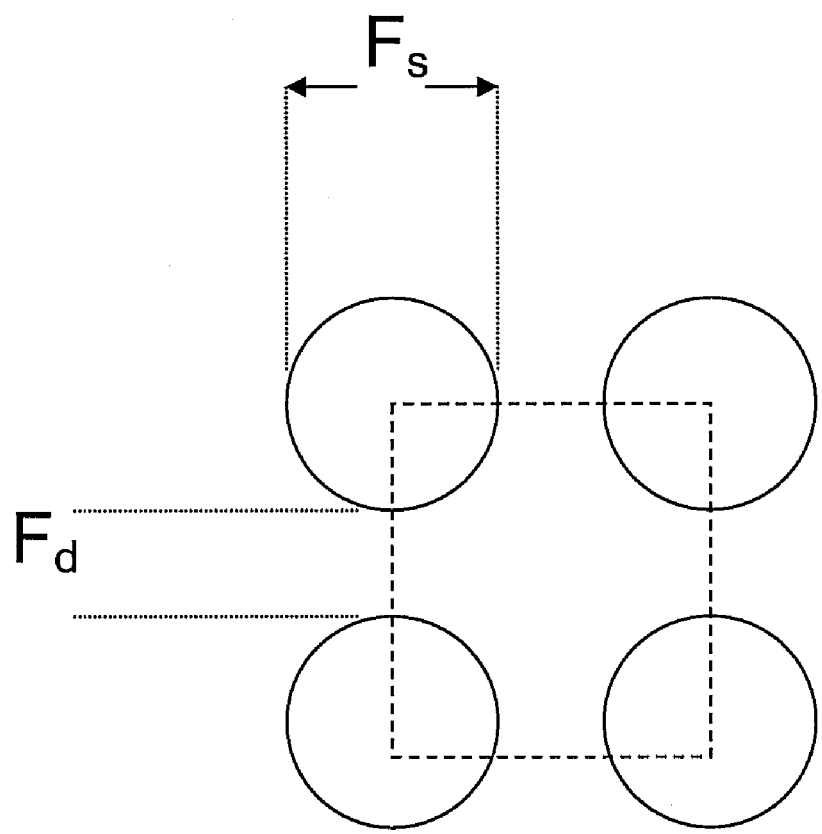
FIG. 9 depicts a unit of four adjacent circular spots arranged on the support member according to the present invention.

FIG. 9 depicts a unit of four adjacent circular spots which are of equal functional size Fs. For a circular spot, the functional size Fs is the diameter of the spot. The functional width defines the smallest amount of a circular area on the support member 12 which is capable of delivering an optimal dynamic range of signal. The functional width varies with the density of the receptors 18 and often the occurrence of the second member 20. For the circular spot, Fs is a value in the range of 5 to 100 micrometers, preferably in the range of 20 to 400 micrometers, and more preferably in the range of 40 to 150 micrometers. The functional distance Fd has a value in the range of 10 to 200 percent of that of Fs and preferably in the range of 50 to 150 percent of that of Fs.

A total number of the spots upon which the receptors are deposited varies with the type of the support member 12. In particular instances where the support member 12 is a conventional glass slide (1×3 in) or a nitrocellulose membrane strip of equivalent size, the total number is within the range of 4 to 400, preferably within the range of 8 to 200, and more preferably within the range of 16 to 100.

An inventive analytical system enables an end user to customize and group particular analytes to be detected. A total number of the analytes that are detectable varies with the type of the support member 12. Since conventional microarray applications require a much higher number of analytes, often in the number of 3000 and up and a small group of analytes the versatility is of these microarrays is limited. This limitation is overcome by the present invention in which the identities and the total number of the analytes are determined by the end user. The duplicates of each analyte is aligned as a row or a column on the support member 12 and different rows or columns are grouped so as to be corresponding to a particular experimental variation to a sample wherein the analyte is contained. Due to the versatility of the inventive analytical system, the end user is able to construct different systems corresponding to respective metabolic research needs. An exemplary list of groups of analytes includes those detecting glycolysis, citric acid cycle, pentose phosphate pathway, glycogen biosynthesis, galactose pathway, beta-oxidation pathway, cholesterol biosynthesis, urea cycle, amino acid metabolism, oxidative phosphorylation, cell cycle, signaling pathway, and blood coagulation pathway. Analytes involved in one of more of above biomedical pathways are included on a support member 12. Optionally an internal control with duplication is included in each system so that data generated thereto is comparable to one another.

A commercial reagent package according to the present invention contains a support derivatized as detailed herein, along with peroxidase, enzyme, coupling agent, and labeling agent reagents. Instructions are supplied to perform the inventive amplified detection as detailed herein.

The methodology of the present invention may be implemented in accord with various array-based analyses of the type shown in the prior art including both layered and non-layered assays and incorporated hereinabove by reference. Specific chemistries for the catalysts, supports, substrates, labels and members of the specific binding pair will depend upon the exact nature and purpose of the assays, which, in view of the teaching presented herein and in the patents referred to herein, will be readily apparent to one of skill in the art.

EXAMPLES

Comparison of Direct and Amplified Array Analysis

Example 1

Nucleic Acid Detection

For direct detection, cyanine 5 labeled cDNA was prepared from 100 µg and 4 µg Jurkat total RNA using the MICROMAX Direct Reagent Kit (NEN Life Science Products, Boston, Mass.). The cyanine 5 labeled cDNA was hybridized to Practice Slides (MICROMAX Human cDNA Microarray System I, NEN Life Science Products, Boston, Mass.) according to MICROMAX Human cDNA System I-Direct (NEN Life Science Products, Boston, Mass.) kit directions.

For amplified analysis, biotin labeled cDNA was prepared from 4 µg Jurkat total RNA using the MICROMAX Human cDNA Microarray System I kit reagents and protocols. Hybridization to Practice Slides and amplified detection using streptavidin-HRP and cyanine 5 tyramide were according to the MICROMAX Human cDNA Microarray System I kit directions.

Slides were scanned on a GSI Lumonics ScanArray 5000 (Watertown, Mass.) scanner.

Figure 6A:
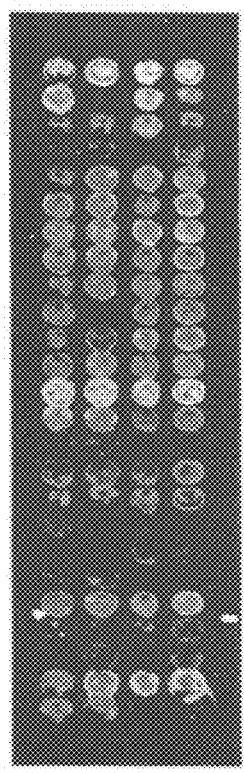
FIGS. 6A-C are reproductions illustrating a comparison of direct and amplified array analysis wherein (A) illustrates the results for direct analysis using 100 μg total RNA, (B) illustrates the results obtained for direct analysis using 4 μg total RNA, and (C) illustrates the results for amplified analysis using 4 μg RNA.
Figure 6B:
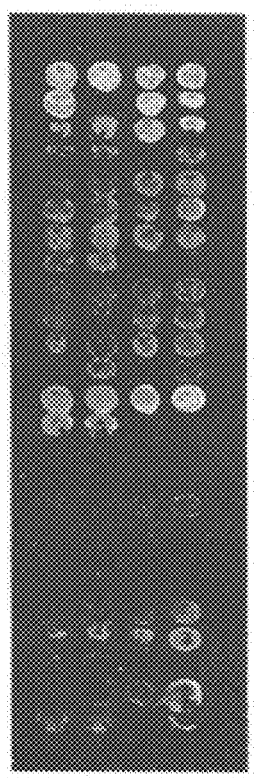
Figure 6C:
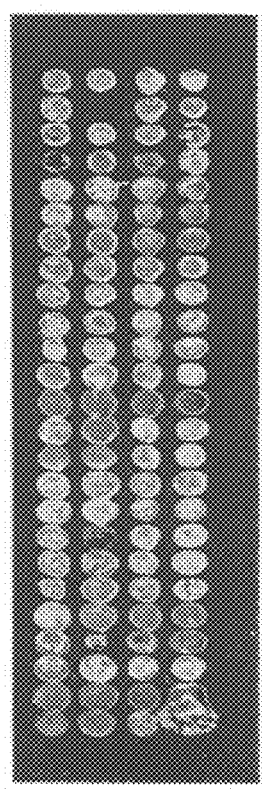

The results for direct analysis using 100 µg total RNA are shown in FIG. 6A. FIG. 6B shows the results obtained for direct analysis using 4 µg total RNA. The results for amplified analysis using 4 µg total RNA is shown in FIG. 6C. The loss of signal going from 100 µg to 4 µg of total RNA for direct analysis indicates that there is insufficient material available for adequate analysis. A greater amount of cells or tissue mass is required for the direct method. The signal for the inventive amplified analysis using 4 μg of total RNA is greater than that using 100 μg for direct analysis, allowing for much greater flexibility in analyzing small amounts of tissues or cells.

Example 2

Protein Detection

Aminosilane slides (Erie Scientific, Portsmouth, N.H.) were spotted with a mouse monoclonal antibody and streptavidin. For spotting, serial two-fold dilutions were made of each protein starting at 100 ug/ml in phosphate buffered saline (PBS). Slides were washed in PBS containing 0.1% Tween 20 (Sigma, St. Louis, Mo.) and blocked for 30 minutes with PBS, 0.1% Tween 20, 0.5% Bovine Serum Albumin (BSA, Sigma). The slides were then incubated for 30 minutes with Goat anti-Mouse Biotin (Sigma) diluted 1/100 in PBS, 0.1% Tween 20, 0.5% BSA and washed three times with PBS, 0.1% Tween 20.

For conventional detection, slides were incubated for 30 minutes with Streptavidin-Cy3 (Jackson ImmunoResearch, West Grove, Pa.) diluted 1:100 in PBS, 0.1% Tween 20, 0.5% BSA and washed three times with PBS, 0.1% Tween 20. The slides were rinsed in water and air dried.

For inventive amplified detection, slides were incubated for 30 minutes with Streptavidin-HRP (PerkinElmer Life Sciences, Boston, Mass.) diluted 1/100 in PBS, 0.1% Tween 20, 0.5% BSA and washed three times with PBS, 0.1% Tween 20. The slides were then incubated for ten minutes with Biotinyl-Tyramide diluted 1/500 in Amplification Diluent (ELAST Kit, PerkinElmer Life Sciences) containing 2.5 M NaCl, and washed three times with PBS, 0.1% Tween 20. Slides were incubated for 30 minutes with Streptavidin-Cy3 diluted 1:200 in PBS, 0.1% Tween 20, 0.5% BSA and washed three times with PBS, 0.1% Tween 20. The slides were rinsed in water and air dried.

Slides were scanned with a Packard (Downers Grove, Ill.) ScanArray 5000 scanner.

Figure 7:
FIG. 7 is a prior art detection slide of mouse monoclonal antibody (top) and streptavidin.
Figure 8:
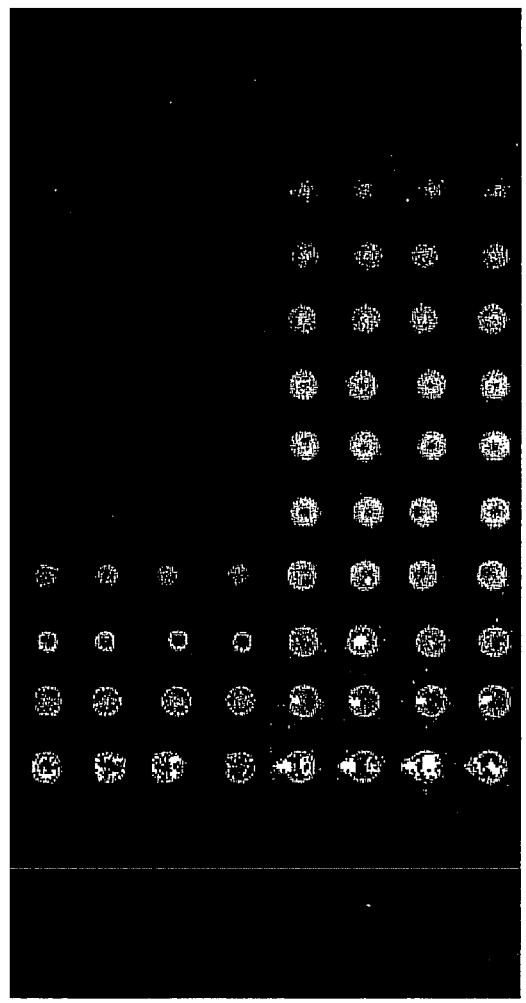
FIG. 8 is an amplified detection slide, of mouse monoclonal antibody (top) and streptavidin.

The results for conventional direct analysis for a quadruplet dilution series of mouse monoclonal antibody (top) and streptavidin (bottom) visualized with anti-mouse IgG biotin and streptavidin Cy3 are shown in FIG. 7. The results of the inventive amplified detection for the same quadruplet dilution series as per FIG. 7 are shown in FIG. 8. Inventive detection is visualized with anti-mouse IgG biotin, streptavidin-HRP, biotinyl-tyramide and streptavidin Cy3. The inventive amplified detection is approximately 64 to 128 times more sensitive and approximately 32 times more sensitive for immobilized mouse monoclonal antibody and streptavidin, respectively, as compared to conventional direct detection.

Example 3

Cell Lysate Detection

Aminosilane slides (Erie Scientific, Portsmouth, N.H.) are spotted with an array of antibodies targeted to yeast proteins. Each antibody is spotted at a predetermined optimal concentration in phosphate buffered saline (PBS). Slides are washed in PBS containing 0.1% Tween 20 (Sigma, St. Louis, Mo.) and blocked for 30 minutes with PBS, 0.1% Tween 20, 0.5% Bovine Serum Albumin (BSA, Sigma).

Yeast cell lysate is prepared by incubating the cells in a sodium acetate buffer, pH 5.0, containing 15% CHAPS (Sigma), 8 M Urea (Sigma), 5 mM EDTA (Sigma) and 4 mM TCEP (Pierce, Rockford, Ill.). The pH is adjusted by adding 10 μl of 1 M BisTris-HCl buffer pH 6.5 per 100 μl lysate. To label the proteins with biotin, 15 μl of 0.1 M N-(biotinoyl)-N'-(iodoacetyl) ethylenediamine (Molecular Probes, Eugene, Oreg.) in dimethylsulfoxide (Aldrich, Milwaukee, Wis.) is added per 100 μl lysate and incubated for 60 min. at ambient temperature. Reagents are removed by dialysis against PBS.

Alternately, yeast cell lysate is prepared by suspending the cells in sodium acetate buffer, pH 5.0. The cells are disrupted using glass beads and a Mini-BeadBeater (BioSpec Products, Bartlesville, Okla.) according to the manufacturer's directions. Cell debris is removed by centrifugation for 15 min. at 12000×g. The extracted proteins are reduced with 4 mM TCEP, and the pH is adjusted by adding 10 μl of 1 M BisTris-HCl buffer pH 6.5 per 100 μl lysate. To label the proteins with biotin, 15 μl of 0.1 M N-(biotinoyl)-N'-(iodoacetyl) ethylenediamine (Molecular Probes, Eugene, Oreg.) in dimethylsulfoxide (Aldrich, Milwaukee, Wis.) is added per 100 μl lysate and incubated for 60 min., and the lysate is dialyzed against PBS.

The slides are incubated for 60 minutes with the labeled cell lysate and washed three times with PBS, 0.1% Tween 20.

For standard detection, slides are incubated for thirty minutes with Streptavidin-Cy3 (Jackson ImmunoResearch, West Grove, Pa.) diluted 1:100 in PBS, 0.1% Tween 20, 0.5% BSA and washed three times with PBS, 0.1% Tween 20. The slides are rinsed in water and air dried.

For amplified detection, slides are incubated for 60 minutes with Streptavidin-HRP (PerkinElmer Life Sciences, Boston, Mass.) diluted 1/100 in PBS, 0.1% Tween 20, 0.5% BSA and washed three times with PBS, 0.1% Tween 20. The slides are then incubated for ten minutes with Biotinyl-Tyramide diluted 1/500 in Amplification Diluent (ELAST Kit, PerkinElmer Life Sciences) containing 2.5 M NaCl, and washed three times with PBS, 0.1% Tween 20. Slides are incubated for thirty minutes with Streptavidin-Cy3 diluted 1:200 in PBS, 0.1% Tween 20, 0.5% BSA and washed three times with PBS, 0.1% Tween 20. The slides are rinsed in water and air dried.

Slides are scanned with a Packard (Downers Grove, Ill.) ScanArray 5000 scanner. Results were comparable to those detailed with respect to Example 2.

The foregoing drawings, discussion and description are illustrative of the general principles of the present invention, and some specific embodiments thereof, but are not meant to be limitations upon the practice of the present invention, since numerous modifications and variations will be readily apparent to one of skill in the art. It is the following claims, including all equivalents, which define the scope of the invention.

The invention claimed is:

1. An analytical system comprising:
a support member having a plurality of chemically active receptors thereupon, wherein said receptors are grouped within an array of spots, said spots with a functional size of 5 micrometers to 400 micrometers, said spots separated with a functional distance from each other, wherein said functional distance is 10 to 200 percent in value of the diameter of said spots;
each of said spots comprising at least one of a plurality of different first members each immobilized on an uppermost surface of said support, said first members being selected from the group consisting of: protein, peptide, polysaccharide, cell fragments, cells, tissue, organometallics, metal ion chelating organic ligands, and combinations thereof, said first members each being capable of binding to a member of a plurality of different complementary second members to form a specific binding pair;

a peroxidase enzyme; and a conjugate of a label and a substituted phenol substrate for said enzyme, said substrate being activatable by said enzyme so as to cause said substrate to bind to one of said chemically active receptor sites whereby said substrate and said label are immobilized upon said support member.

2. An analytical system as in claim 1, further comprising a coupling agent operative to couple said enzyme to the second member of said specific binding pair.

3. An analytical system as in claim 2 wherein said coupling agent functions absent an antibody/antigen association.

4. An analytical system as in claim 1, wherein said peroxidase enzyme comprises horseradish peroxidase.

5. An analytical system as in claim 1, wherein said substituted phenol substrate comprises tyramine.

6. An analytical system as in claim 1, wherein said labeling agent comprises a fluorescent cyanine dye.

7. An analytical system as in claim 1, wherein said different first members of said specific binding pair comprise peptides.

8. An analytical system as in claim 1, wherein said different first members of said specific binding pair comprise polysaccharide.

9. An analytical system as in claim 1, wherein said different first members of said specific binding pair comprise cells.

10. An analytical system as in claim 1, wherein said different first members of said specific binding pair comprise cell fragments.

11. An analytical system as in claim 1, wherein said different first members of said specific binding pair comprise tissues.

12. An analytical system as in claim 1, wherein said different first members of said specific binding pair comprise organometallic.

13. An analytical system as in claim 1, wherein said different first members of said specific binding pair comprise metal ion chelating organic ligand.

14. The system of claim 1 wherein said support comprises glass.

15. A commercial reagent package comprising a substantially planar support member having a plurality of receptor sites thereon, wherein said receptor sites are grouped within an array of spots, said spots having a functional size from about 10 to 400 micrometers, said spots separated with a functional distance from each other wherein said functional distance is 10 to 200 percent in value of the diameter of said spots;
  at least one of a plurality of different first members capable of forming a specific binding pair and immobilized on an uppermost surface of said support within one of said spots, said first members being selected from the group consisting of: protein, peptide, polysaccharide, cell fragments, cells, tissue, organometallics, metal ion chelating organic ligands, DNA, cDNA, RNA, oligonucleotides and combinations thereof;
  a peroxidase enzyme;
  a coupling agent operative to couple said enzyme to said specific binding pairs;
  a conjugate of a label and a substituted phenol substrate for said enzyme; and
  instructions for the use thereof as an analytical system for a second member capable of being bound to said first members to form said specific binding pairs.

16. A commercial reagent package of claim 15 wherein said coupling agent functions absent an antibody/antigen association.

17. The package of claim 15 wherein said support comprises glass.

* * * * *

UNITED STATES PATENT AND TRADEMARK OFFICE
CERTIFICATE OF CORRECTION

PATENT NO. : 8,153,367 B2
APPLICATION NO. : 11/741548
DATED : April 10, 2012
INVENTOR(S) : Mark Norman Bobrow et al.

Page 1 of 1

It is certified that error appears in the above-identified patent and that said Letters Patent is hereby corrected as shown below:

Column 4, Line 66, After only Delete "a"

Column 6, Line 16, After one Delete "of"

Column 7, Line 43, Delete "streptavidin Cy3"

Column 7, Line 47, Delete "streptavidin Cy3" Insert --Streptavidin-CY3--

Signed and Sealed this
Twenty-eighth Day of August, 2012

David J. Kappos
*Director of the United States Patent and Trademark Office*